United States Patent [19]

Maxim et al.

[11] Patent Number: 4,617,262
[45] Date of Patent: Oct. 14, 1986

[54] ASSAYING FOR CIRCULATING IMMUNE COMPLEXES WITH LABELED PROTEIN A

[75] Inventors: Peter E. Maxim, Downingtown; Robert W. Veltri, West Chester, both of Pa.

[73] Assignee: CooperBiomedical, Inc., Palo Alto, Calif.

[21] Appl. No.: 516,465

[22] Filed: Jul. 22, 1983

[51] Int. Cl.$^4$ .................. G01N 33/53; G01N 33/535; G01N 33/539
[52] U.S. Cl. .......................................... 435/7; 435/28; 436/506; 436/507; 436/539; 436/828
[58] Field of Search ............... 436/506, 507, 828, 539; 435/7, 28

[56] References Cited

U.S. PATENT DOCUMENTS 3,850,798  11/1974  Sjöquist ............................ 210/31 C
3,995,018  11/1976  Sjöquist ............................... 424/1.5
4,332,783   6/1982  Pernice ........................... 436/528 X

OTHER PUBLICATIONS

Ritzmann, S., et al., "Immune Complexes...," Clinical Chemistry 28 (6), 1259-1271 (1982).
Stevens, W., et al., "A Method for Rapid Determination of IgG-Containing...," Immunology Letters 3, 1-4 (1981).
Dobre, M., et al., "Detection of Circulating Immune Complexes...," Rev. roum. Biochim. 19 (2), 115-120 (1982).
Faiferman, I., et al., "Staphylococcal Protein A Fluoroimmunoassay...," Arthritis and Rheumatism 25 (7), 799-801 (1982).
Hallgren, R., et al., "Detection of Circulating IgG Aggregates..." Ann. rheum. Dis. 35, 306-313 (1976).

Primary Examiner—Sidney Marantz
Attorney, Agent, or Firm—Vorys, Sater, Seymour and Pease

[57] ABSTRACT

A method for assaying circulating immune complexes comprises
   contacting the circulating immune complexes in solution in serum with a staphylococcal protein-A linked to a detectable label, whereby a CIC-protein-A-label complex is formed,
   selectively precipitating the CIC-SPA-label complex by contacting the complex with polyethylene glycol,
   separating the precipitated CIC-SPA-label complex from the serum,
   measuring the quantity of the label in the precipitated CIC-protein-A-label complex
   comparing the measured quantity of label with at least one standard prepared by subjecting a solution containing a known amount of CIC or functional equivalent material to the same assay. The method requires only a single precipitation step and in a preferred embodiment the formation of the CIC-SPA-label complex may be formed in a single step.

21 Claims, No Drawings

ASSAYING FOR CIRCULATING IMMUNE COMPLEXES WITH LABELED PROTEIN A

BACKGROUND OF THE INVENTION

1. Field of the invention:

This invention relates to methods of analyzing for circulating immune complexes in mammalian blood serum and more particularly to methods of analyzing for circulating immune complexes using an enzyme-linked immunoassay.

2. Description of the prior art:

Macromolecular circulating immune complexes (CIC) are formed in the blood serum of mammals by the interaction of endogenous or exogenous antigens and specific antibodies formed against these antigens by the host. Typical exogenous antigens which provoke the formation of antibodies include antigens asociated with infectious agents such as viruses, bacteria, parasites and fungi, as well as drugs, foods, and allergens. Typical endogenous antigens include cellular antigens such as ribosomes, nucleic acid, nucleoproteins, cell surface antigens, mitochondria and the like, and plasma factors such as rheumatoid factor, thyroglobulin, and tumor-associated antigens (e.g., carcinoembryonic antigen) and the like. These macromolecular complexes are removed from circulation under normal circumstances by a complement-dependent phagocytotic process or by deposition in specialized vasculature of kidneys, arteries, skin, lungs, joints and the choroid plexus. The glomerulus of the kidney is very prominent in removal of CIC from the blood. Often CIC can be demonstrated in normal healthy individuals immediately after eating or in normal as well as preeclamptic pregnancies.

The processing of immune complexes by the host can also result in immunopathology such as acute and chronic glomerulonephritis, vasculitis, pancreatitis, hepatitis, serum sickness, and the like, in both man and other mammals. Hence, it is desirable to have a method for determining the concentration of CIC in humans and other animals.

A number of methods of analyzing for CIC have been developed. Physical methods such as analytical ultracentrifugation, gel filtration, sucrose density gradient centrifugation, ultrafiltration, electrophoresis and nephelometry have been used. Chemical methods such as precipitation with polyethylene glycol and cryoprecipitation have also been used. Cellular methods depending on the interaction of CIC with Fc-receptors (FcR) in the cell membrane, such as platelet aggregation, Raji cell assay, rosette inhibition, release of soluble enzymes by eosinophils and basophils, and the bull sperm agglutination assay, have been used. Immunologic detection methods for CIC include competitive assays, complement dependent assays, antiglobulin methods and binding to staphylococcal protein-A. A review of prior assay methods for CIC is found in Ritzmann, S. E., and Daniels, J. C., Clinical Chemistry 28(6), 1259-1271 (1982).

The very existence of many methods of assaying CIC is an indication that a completely satisfactory method is not yet available. Problems involved in collecting, processing and storing the sera to be assayed, the stability of standards, ease of performance of the particular assay, and reproducibility of results are all factors to be considered in evaluating the suitability of a particular assay. A collaborative study conducted by the World Health Organization (WHO) has substantiated the importance of these problems and concluded that no single test is a valid CIC assay (Lambert, P. H., et al., J. Clin. Lab. Immunol. 1, 1-15 (1978).

A number of assays have been devised which depend on the precipitation of the CIC by polyethylene glycol (PEG), followed by reaction with staphylococcal protein-A (SPA).

Hallgren, R., et al., Ann. rheum. Dis. 35, 306-313 (1976) disclose assaying CIC by first separating CIC from the other proteins in the serum by exclusion chromatography on a polysaccharide gel and then precipitating with radiolabeled staphylococcal protein-A in the presence of polyethylene glycol. The excess reagent is separated and the radioactivity of the precipitated CIC is measured by counting in the usual way.

Stevens, W., et al., Immunology Letters 3, 1-4 (1981) disclose an assay for CIC wherein the complexes are first selectively precipitated by 5% polyethylene glycol and separated from the non-aggregated immunoglobulins. The CIC are then resuspended and reprecipitated with radiolabeled SPA, and quantitated in the usual way by counting.

Dobre, M., et al., Rev. roum. Biochim. 19 (2), 115-120 (1982) disclose an assay wherein CIC are first selectively precipitated with polyethylene glycol, then reprecipitated on *Staphylococcus aureus*. The precipitated CIC are then incubated with radiolabeled SPA, the excess reagent is removed, and the CIC are quantitated by counting.

Faiferman, I., et al., Arthritis and Rheumatism 25 (7), 799-801 (1982) disclose a fluoroimmunoassay for CIC wherein the complexes are first selectively precipitated with a 2.5% solution of polyethylene glycol, then resuspended and contacted with a solution of SPA linked to a fluorescent label, whereby a complex of CIC and fluorescent labeled SPA is formed. The complex is again precipitated with polyethylene glycol, the excess reagent is removed, and the fluorescence of the bound reagent is measured with a spectrofluorometer. Faiferman et al. disclose that the label used on the SPA could also be an enzyme label.

In all of these assays for CIC a preliminary separation of the CIC from the other proteins in the serum, particularly from the immunoglobulins, which also bind to SPA, is performed. Therefore, these assays involve at least two precipitation steps.

Hence a need has continued to exist for a simpler and more rapid assay for CIC, based on the binding of CIC to SPA, which avoids the disadvantages of the known assays, and in particular for an assay for CIC which does not require a preliminary separation of CIC from other serum proteins.

SUMMARY OF THE INVENTION

Accordingly, it is an object of the invention to provide a method for assaying circulating immune complexes in mammalian serum.

A further object is to provide a method for assaying CIC in mammalian serum by means of a label immunoassay.

A further object is to provide a method for assaying CIC in mammalian serum by means of an enzyme-linked immunoassay.

A further object is to provide a method for assaying CIC using staphylococcal protein-A which does not require a preliminary separation of CIC from uncomplexed immunoglobulins.

A further object is to provide an immunoassay for CIC in mammalian serum having a single precipitation step.

A further object is to provide an analytical reagent specially adapted for an immunoassay for CIC in mammalian serum having a single precipitation step.

Further objects of the invention will become apparent from the description of the invention which follows.

The objects of the invention are attained by a method for assaying circulating immune complexes which comprises contacting the circulating immune complexes in solution in serum with staphylococcal protein-A linked to a detectable label, whereby a CIC-protein-A-label complex is formed, selectively precipitating said CIC-SPA-label complex by contacting the complex with polyethylene glycol, separating the precipitated CIC-SPA-label complex from the serum, measuring the quantity of label present in the precipitate, and comparing the measured quantity of label with at least one standard prepared by subjecting a solution containing a known amount of CIC or functional equivalent material to the same assay.

DETAILED DESCRIPTION OF THE INVENTION AND PREFERRED EMBODIMENTS

The assay of this invention is based upon the discovery that SPA binds preferentially to CIC. This preferential binding affinity allows conditions to be selected wherein the CIC can be bound to SPA and precipitated without preliminary separation of CIC from uncomplexed immunoglobulins. Accordingly, it is possible to eliminate the preliminary separation step used in assays of the prior art and conduct the assay in a single tube with a single precipitation step. This materially simplifies the assay and is therfore a substantial improvement over the known assays for CIC.

According to the assay of the invention, the serum containing CIC and uncomplexed immunoglobulins is mixed with a solution containing SPA labeled with a suitable label such as an enzyme, a radioactive label or a fluorescent label and incubated for a period of time sufficient to form a CIC-SPA-label complex. The conditions may be chosen so that the CIC-SPA-label complex is formed while no substantial amount of complex between labeled SPA and uncomplexed immunoglobulins is formed. The conditions favorable for this result are a temperature between about 18° C. and about 25° C., preferably about 20° C., an amount of SPA-label in excess of that required for binding all the CIC, and an incubation time sufficient for the completion of complex formation. It has been found that the reaction is essentially complete in about 15 minutes.

The CIC-SPA-label complex is then precipitated by addition of a solution, preferably an aqueous solution, of polyethylene glycol, to produce a final concentration of PEG in the analytical solution of between 2.0% and 3.5%, by weight. Preferably the concentration of PEG in the analytical solution is about 3.5% by weight. The mixture is then incubated at a temperature between about 4° C. and about 8° C., preferably about 4° C., for a period of time to assure that the precipitation is complete enough to serve for analytical purposes. It has been found that the precipitation is complete enough for quantitative assay after about 3–4 hours; however, the incubation can be continued for as long as 18 hours if desired. The polyethylene glycol used in the precipitation step should have a molecular weight such that it is capable of inducing precipitation of the CIC-SPA-label complex. A suitable polyethylene glycol is one having a molecular weight between about 6000 and about 8000. Preferably polyethylene glycol having an average molecular weight of about 6000 (PEG-6000) is used The precipitated CIC-SPA-label complex is then washed, e.g., with an aqueous solution of polyethylene glycol, to remove all traces of the serum and unreacted SPA-label.

The measurement of the amount of label present in the CIC-SPA-label complex is conducted by a technique appropriate to the type of label used. For example, if a radioactive label has been attached to the SPA the amount of radiolabel in the precipitate can be determined by direct counting of radioactive decays per unit time in the conventional manner. If a fluorescent label has been used, the fluorescence of the precipitated material is determined, usually by resuspending the precipitate and measuring the fluorescent intensity in a spectrofluorometer.

A preferred label is an enzyme label. When an enzyme label has been used, the CIC-SPA-enzyme complex is then contacted with a substrate for the enzyme, e.g., by resuspending the precipitated CIC-SPA-enzyme complex in an aqueous solution of the enzyme substrate. Enzymatic conversion of the substrate is allowed to proceed for a predetermined period of time and the reaction is then terminated. The amount of substrate converted is then measured to determine the amount of CIC-SPA-enzyme complex present. A standard series of sera having known amounts of CIC or functionally equivalent material, i.e., a material which undergoes the same reaction as CIC with SPA, is run to establish a calibration curve for the assay under particular conditions. A plot of concentration versus optical absorbance is made for the series of standards and a smooth curve is drawn through the plotted data points. The sample sera are then assayed under the same conditions and the concentration of CIC in the serum is determined by comparison with the calibration curve, as is well known to those skilled in the art.

When a radiolabel or a fluorescent label is employed, a series of standards is prepared and a calibration curve is prepared in the same manner.

For a calibration standard an aggregated IgG may be used. This material binds to SPA just as CIC and is therefore functionally equivalent. It is convenient to prepare such a standard by heat aggregation of IgG, e.g., by heating a solution of IgG to a temperature of 62° C. An artificial immune complex standard can also be prepared by reacting an antigen with an antibody IgG to the antigen to form an immune complex.* *Also, sera from patients with immune complex diseases (RA, SLE etc.) may serve as a source of naturally occurring immune complex standards. It has been found that the immune complex standards are fully equivalent to the heat-aggregated immunoglobulin standard. This discovery has made it possible to prepare specific standards for use in assays for CIC in different species of animals. Furthermore, since the SPA binding sites of the CIC are expected to resemble those of the antigen-antibody complexes more closely than those of the heat aggregated immunoglobulins, standards based on artificial immune complexes may contribute to more accurate assays.

The enzyme used in the assay of the preferred embodiment of this invention may be any enzyme which can convert a substrate to provide a detectable amount of substrate conversion. Preferred enzymes are those which can react with a substrate to produce a colored substance or a substance which can react to yield a colored substance which can then be quantitated by conventional absorption spectrophotometry. Suitable enzymes include alkaline phosphatase, galactosidase, glucose oxidase, horeseradish peroxidase and the like. A preferred enzyme is horseradish peroxidase.

The enzyme is conjugated to the SPA by conventional procedures, e.g., by treatment of the SPA with glutaraldehyde followed by reaction with the enzyme. Typical conjugation procedures are disclosed in Avrameas, S., Immunochemistry 6, 43–52.

When horseradish peroxidase is used as the enzyme label the substrate used may be an aqueous solution of hydrogen peroxide containing 2,2′-azino-di-(3-ethylbenzothiazoline sulfonic acid) (ABTS). This mixture develops a color which can be quantitated by measuring the absorption of the solution at a wavelength of 410 nm ($A_{410}$).

In practicing the assay of this invention it is possible to add the serum containing CIC to be quantitated to the SPA-label solution in the form of a diluted serum, e.g., in a 1:40 solution, as is conventional in assays of this type. However, it is also possible to add the serum to be assayed directly to the reagent without preliminary dilution. This procedure further simplifies the assay of this invention.

In a preferred embodiment of the invention, the formation of the CIC-SPA-label complex and its precipitation from the serum can be performed in a single step. In this embodiment an solution of SPA-label and polyethylene glycol is mixed with the serum containing CIC and incubated for five to fifteen minutes at a temperature of about 18° C. to 25° C. followed by incubation for three to four hours at a temperature of about 4° C. to about 8° C. Preferably the mixture is incubated for about 15 minutes at room temperature followed by incubation for 3–4 hours at about 4° C. Under these conditions the CIC-SPA-label complex forms and is precipitated. After the precipitated complex is washed, the amount of label present in the precipitate is determined. For example, if an enzyme label is used, the precipitate is incubated with a solution of the enzyme substrate for a predetermined period of time and the amount of enzymatic conversion which takes place is determined as discussed above.

In this preferred embodiment of the invention the reagent used is preferably a solution comprising the SPA-label, in particular the SPA-enzyme, reagent in aqueous solution in a borate buffer (pH = 8.0–8.4) containing about 3.5% by weight of polyethylene glycol. The preparation of this solution is somewhat critical. Example 1 below provides directions for preparing this reagent for optimum effectiveness.

The invention will be illustrated by the following examples which are not intended to limit its scope.

EXAMPLE 1.

This example illustrates the preparation of the reagent used in the preferred embodiment of this invention.

A solution was prepared by mixing the following ingredients:
70 ml distilled water
18 ml borate buffer concentrate (0.1 M sodium borate, pH=8.4)
10 ml PEG concentrate (35% by weight of polyethylene glycol having an average molecular weight of 6000, dissolved in 0.1 M sodium borate buffer solution)
2 ml protein-A-horseradish peroxidase concentrate It is critical that the ingredients be mixed in the order recited. The concentration of the SPA-peroxidase solution to be used is determined by titrating the product of the SPA-horseradish peroxidase conjugation reaction, and adjusting the concentration of the solution used in preparing the reagent so that the volume of reagent used in the assay contains an excess of SPA-peroxidase.

EXAMPLE 2.

This example illustrates the analysis of CIC in serum using the preferred embodiment of the method of this invention.

Immune complexes to serve as standards were prepared by incubation of human albumin (1:8 dilution of 20 mg/ml) and anti-human albumin (Cappel Laboratories) overnight at 4° C. Following the overnight incubation, the solution was centrifuged at 2600 RPM for 20 minutes at room temperature to remove any precipitated protein.

A series of 12×75 mm glass test tubes was prepared for the standard curve, a blank and a sample as follows: one tube for the blank, five standards labeled 40, 20, 10, 5 and 2.5 micrograms equivalent per milliliter, and one tube for the sample.

Dilutions of 1:40 of the sample and the standard were prepared in separate tubes.

One hundred microliters of borate buffer (0.1 M sodium borate, pH=8.4) were pipetted into the blank tube and the standards labeled 20, 10, 5, and 2.5 micrograms equivalent per milliliter.

One hundred microliters of diluted standard were pipetted into the tubes labeled 40 and 20 micrograms equivalent per milliliter. Serial doubling dilutions were performed by transferring 100 microliters of solution from standard tube 20 to standard tube 10, mixing, transferring 100 microliters from standard tube 10 to standard tube 5, mixing, transferring 100 microliters of solution from standard tube 5 to standard tube 2.5, mixing and, finally, discarding 100 microliters from standard tube 2.5.

One hundred microliters of the diluted serum sample were pipetted into the sample tube.

Into each tube was pipetted 0.9 ml of the reagent of Example 1 comprising a solution of protein-A conjugated to horseradish peroxidase in a 3.5% aqueous solution of polyethylene glycol having an average molecular weight of 6000 (PEG-6000). The solutions were mixed well and the reaction mixtures were incubated at room temperature for 15 minutes followed by 3 hours incubation at 4° C.

The tubes were centrifuged at 800×g for 30 minutes, the supernatant was carefully decanted and the tubes were inverted and blotted on absorbent paper to remove excess fluid, using great care to avoid disrupting the pellet at the bottom of the tube.

The pellet was washed twice by mixing with 1.5 ml of wash solution at room temperature, centrifuging at 800×g for 30 minutes and carefully decanting the supernatant and drying as described above.

Then 2.0 ml of a solution of 2,2′-azino-di-(3-ethylbenzothiazoline sulfonic acid) in an aqueous solution of hydrogen peroxide were added to each tube, the solutions were mixed well and the tubes were incubated at room temperature for 30 minutes. Thereafter, 0.05 ml of a 0.05% aqueous solution of sodium azide, which terminates the reaction, is added to each tube and the absorbance of each solution is read at a wavelength of 410 nm using a spectrophotometer.

The absorbance at 410 nm ($A_{410}$) is plotted on arithmetic graph paper versus the concentration for all the standards. The concentration of the immune complex in the sample can then be determined by reading off the plot the concentration of immune complex which gives the measured $A_{410}$. This value when multiplied by 40 (the degree of dilution) yields the value of micrograms equivalent per milliliter of aggregated IgG in the serum sample.

EXAMPLE 3

This example illustrates the binding of protein-A-peroxidase to native and heat aggregated IgG.

A solution of IgG (human) was heat aggregated at 62° C. and then fractionated by exclusion chromatography on a polysaccharide gel column (Sephadex G-200, manufactured by Pharmacia AB) to separate native and aggregated IgG. Each fraction was concentrated to the same protein concentration and serial dilutions were made to provide a series of samples having varying concentrations of aggregated and native IgG as indicated in Table 1 below. Each of the samples was analyzed by the procedure of Example 2 and the optical absorbance at 410 nm is tabulated in Table 1.

TABLE 1

| Protein | $A_{410}$ | |
|---|---|---|
| micrograms/ml | Aggregated | Native |
| 40 | 1.128 | 0.146 |
| 20 | 0.581 | 0.098 |
| 10 | 0.284 | 0.033 |
| 5 | 0.120 | 0.010 |
| 2.5 | 0.022 | 0.000 |

The results as shown in the table indicate preferential binding of the protein-A-peroxidase to the heat aggregated IgG rather than to the native (non-denatured) IgG.

EXAMPLE 4.

This example illustrates the preparation of an alternative standard material using artificially prepared immune complexes.

Immune complexes were prepared by incubation of human albumin (1:8 dilution of a 20 mg/ml solution) and anti-human albumin (supplied by Cappel Laboratories) overnight at 4° C. Following the overnight incubation, the solution was centrifuged at 2600 RPM for 20 minutes at room temperature to remove precipitated protein. Serial doubling dilutions of the supernatant were made to yield a series of samples having varied concentration of the immune complex as listed in Table 2 below.

TABLE 2

| Dilution | $A_{405}$ (mean determinations) |
|---|---|
| 1:1 | 1.488 |
| 1:2 | 1.034 |
| 1:4 | 0.513 |
| 1:8 | 0.205 |
| 1:16 | 0.086 |
| 1:32 | 0.038 |
| 1:64 | 0.019 |

TABLE 2-continued

| Dilution | $A_{405}$ (mean determinations) |
|---|---|
| Control | 0.001 |

These results show that an artificially prepared immune complex can function as a standard for the assay of CIC just as IgG aggregates prepared by heating.

The reagents for conducting the immunoassay of the invention may conveniently be supplied to the analyst in the form of a kit for assaying circulating immune complexes in mammalian serum comprising at least one container containing a reagent comprising staphylococcal protein-A covalently bound to a detectable label, at least one container containing polyethylene glycol, and at least one container containing a known amount of a calibrating reagent which undergoes the same reaction as circulating immune complex to serve as a standard.

The reagents may be supplied in form of solutions of appropriate concentration either for dilution or for direct use in performing the assay. The reagents may also be supplied in the form of solids ready for dissolving by adding water or a buffer to the containers. For practicing the preferred embodiment of the invention wherein the formation of the CIC-SPA-label complex and its precipitation are performed using a single combined reagent, the SPA-label and the polyethylene glycol may be combined in one container either in form of solids ready for dissolving or in the form of a solution ready for dilution or for direct use in the assay.

Having now fully described the invention it will be apparent to one of ordinary skill in the art that many variations may be made therein without departing from the scope and spirit of the invention.

What is claimed as new and sought to be protected by letters patent of the United States is:

1. A method for assaying circulating immune complexes in mammalian serum which comprises
   (a) contacting said circulating immune complexes in solution in said serum with a staphylococcal protein-A(SPA) linked to a detectable label, whereby a CIC-protein-A-label complex is formed,
   (b) selectively precipitating said CIC-SPA-label complex by contacting the complex with polyethylene glycol,
   (c) separating said precipitated CIC-SPA-label complex from said serum,
   (d) measuring the quantity of said label present in said precipitate, and
   (e) comparing the measured quantity of the label with at least one standard prepared by subjecting a solution containing a known amount of CIC or functional equivalent material to the same assay.

2. The method of claim 1 wherein steps a) and b) are conducted simultaneously by contacting said serum with a solution containing labeled SPA and polyethylene glycol.

3. The method of claim 1 wherein said label is an enzyme label

4. The method of claim 3 wherein said enzyme is horseradish peroxidase.

5. The method of claim 1 wherein said standard is heat aggregated IgG.

6. The method of claim 1 wherein said standard is an immune complex of an antigen and an antibody IgG to said antigen.

7. The method of claim 6 wherein said antigenantibody complex is derived from antigens of the same animal species being assayed.

8. The method of claim 1 wherein said contact with polyethylene glycol is carried out in a solution having a concentration of polyethylene glycol of about 2.0% to about 3.5%, by weight.

9. The method of claim 8 wherein the concentration of polyethylene glycol is about 3.5%, by weight.

10. The method of claim 1 wherein said polyethylene glycol has a molecular weight of about 6000 to about 8000.

11. The method of claim 10 wherein said polyethylene glycol has an average molecular weight of about 6000.

12. A method for assaying circulating immune complexes in mammalian serum which comprises
   (a) contacting said circulating immune complexes in solution in said serum with staphylococcal protein-A (SPA) linked to an enzyme, whereby a CIC-protein-A-enzyme complex is formed,
   (b) selectively precipitating said CIC-SPA-enzyme complex by contacting the complex with polyethylene glycol,
   (c) separating the precipitated CIC-SPA-enzyme complex from said serum,
   (d) contacting the CIC-protein-A-enzyme complex with a substrate for the enzyme for a period of time whereby enzymatic conversion of the substrate takes place,
   (e) measuring the amount of enzymatic conversion which takes place in a predetermined time, and
   (f) comparing the measured amount of enzymatic conversion with at least one standard prepared by subjecting a solution containing a known amount of CIC or functional equivalent material to the same assay.

13. The method of claim 12 wherein steps a) and b) are conducted simultaneously by contacting said serum with a solution containing enzyme-labeled SPA and polyethylene glycol.

14. The method of claim 12 wherein said enzyme is horseradish peroxidase.

15. The method of claim 12 wherein said standard is heat aggregated IgG.

16. The method of claim 15 wherein said standard is an immune complex of an antigen and an antibody IgG to said antigen.

17. The method of claim 16 wherein said antigenantibody complex is derived from antigens of the same animal species being assayed.

18. The method of claim 12 wherein said contact with polyethylene glycol is carried out in a solution having a concentration of polyethylene glycol of about 2.0% to about 3.5%, by weight.

19. The method of claim 18 wherein the concentration of polyethylene glycol is about 3.5%, by weight.

20. The method of claim 12 wherein said polyethylene glycol has a molecular weight of about 6000 to about 8000.

21. The method of claim 20 wherein said polyethylene glycol has an average molecular weight of about 6000.

* * * * *